United States Patent
Bodgan et al.

(10) Patent No.: US 10,562,144 B2
(45) Date of Patent: Feb. 18, 2020

(54) DENTAL MACHINE TOOL

(71) Applicant: Ivoclar Vivadent AG, Schaan (LI)

(72) Inventors: Vadim Bodgan, Pforzheim (DE); Sascha Cramer Von Clausbruch, Mühlacker (DE)

(73) Assignee: Ivoclar Vivadent AG, Schaan (LI)

( * ) Notice: Subject to any disclaimer, the term of this patent is extended or adjusted under 35 U.S.C. 154(b) by 325 days.

(21) Appl. No.: 15/501,889

(22) PCT Filed: Oct. 22, 2015

(86) PCT No.: PCT/EP2015/074467
§ 371 (c)(1),
(2) Date: Feb. 6, 2017

(87) PCT Pub. No.: WO2016/062802
PCT Pub. Date: Apr. 28, 2016

(65) Prior Publication Data
US 2017/0225283 A1    Aug. 10, 2017

(30) Foreign Application Priority Data

Oct. 22, 2014   (EP) ..................................... 14189863

(51) Int. Cl.
*B23Q 11/00* (2006.01)
*B23Q 11/08* (2006.01)
*A61C 13/00* (2006.01)

(52) U.S. Cl.
CPC ...... *B23Q 11/0064* (2013.01); *A61C 13/0003* (2013.01); *B23Q 11/006* (2013.01); *B23Q 11/0891* (2013.01); *Y10T 409/304088* (2015.01)

(58) Field of Classification Search
CPC .............. B23Q 11/0046; B23Q 11/005; B23Q 11/0075; B23Q 11/0064; B23Q 11/006;
(Continued)

(56) References Cited

U.S. PATENT DOCUMENTS 5,153,811 A * 10/1992 Rodrigo ................. H01T 23/00
361/220
8,048,200 B2 * 11/2011 Gefter ..................... B03C 3/017
95/58

(Continued)

FOREIGN PATENT DOCUMENTS

CN        104096696 A    10/2014
DE        19947140 C2    3/2001
(Continued)

OTHER PUBLICATIONS

Machine Translation, Chinese Patent Document, CN104096696, Shan et al. dated Oct. 15, 2014. (Year: 2014).*

*Primary Examiner* — Sunil K Singh
*Assistant Examiner* — Chwen-Wei Su
(74) *Attorney, Agent, or Firm* — Ann M. Knab; Thad McMurray

(57) ABSTRACT

The invention relates to a dental machine tool, in particular a dental milling machine (10), having a tool (12) that is changeable in particular via a tool bank (16), and a workpiece holder (14) for receiving a workpiece such as a dental blank made of ceramic, composite or plastics material such as PMMA, and having a housing (24) which is closable during machining by the machine tool, and having a negative-pressure connection to the housing (24). At least one air nozzle (30) that is fitted on or in the housing (24) is directed towards the workpiece and/or the workpiece holder (14) and/or the tool (12) and/or the tool bank (16) and/or a pane of a front flap of the machine tool. Said air nozzle (30) is equipped with at least one electrode for generating an electric field in the region of the nozzle or in front of the latter, and at least one nozzle comprising at least one electrode is directed towards that side of the workpiece or of the workpiece holder (14) on which the tool (12) machines the workpiece. At least two electrodes of an ionizer extend
(Continued)

in a spaced-apart manner over a substantial part of the housing (24), and as a result of the application of an in particular pulsating AC voltage provides spatial deionization of the air flowing through the housing (24) and/or deionization of the surfaces of the workpiece, workpiece holder (14), tool (12) and/or window (28) and of the chips produced by the machining operation.

27 Claims, 5 Drawing Sheets

(58) Field of Classification Search
CPC ......... B23Q 11/0891; Y10T 409/30392; Y10T 409/304088; A61C 19/007; A61C 13/0004; A61C 1/0007
See application file for complete search history.

(56) References Cited

U.S. PATENT DOCUMENTS

| | | | | |
|---|---|---|---|---|
| 8,764,356 | B2* | 7/2014 | Suyama | B23Q 1/525 408/67 |
| 2013/0244846 | A1* | 9/2013 | Koch | A61C 13/0003 483/16 |
| 2014/0263216 | A1* | 9/2014 | Clark | B23C 1/08 219/121.7 |

FOREIGN PATENT DOCUMENTS

| | | |
|---|---|---|
| DE | 19947140 C2 | 5/2002 |
| DE | 102013005871 A1 | 10/2014 |
| JP | S62284731 A | 12/1987 |
| RU | 2030276 C1 | 3/1995 |
| RU | 2030279 C1 | 3/1995 |

\* cited by examiner

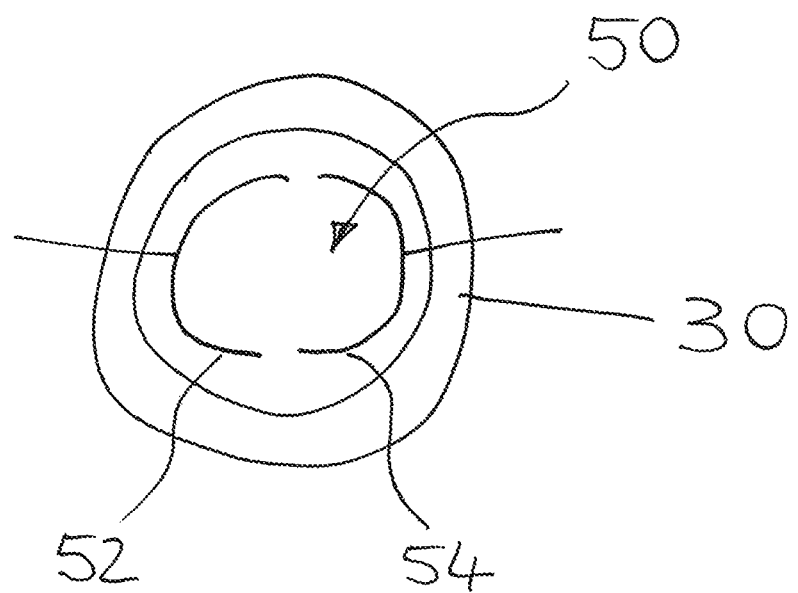

DENTAL MACHINE TOOL

CROSS-REFERENCE TO RELATED APPLICATIONS

This application is a National Stage application of International patent application PCT/EP2015/074467 filed on Oct. 22, 2014 9, 2015, which claims priority to European patent application No. 14189863.5 filed on Oct. 22, 2014, the disclosures of which are incorporated herein by reference in their entirety.

TECHNICAL FIELD

The invention relates to a dental machine tool, in particular a dental milling machine, having a tool that is changeable in particular via a tool bank, and a workpiece holder for receiving a workpiece such as a dental blank made of ceramic, composite or plastics material such as PMMA, and having a housing which is closable during machining by the machine tool.

BACKGROUND OF THE INVENTION

It has been known for a longer time that chips produced in machining processes are ionized by frictional electricity during the machining process. While metallic chips often come into contact with the environment and/or with non-adjacent chips and discharge in this way, this does not hold true for chips made of materials which are not electrically conducting such as glass, ceramic or plastic materials. However, ionization is also observed when materials are machined which are poor conductors such as wood or graphite-reinforced plastics, that is to say plastic materials with embedded electrical conductors.

In order to improve the removal of chips it has become known to equip an air-pressure hose with an electrode which surrounds the aperture of the hose internally and extends around a drill which machines the non-conducting or poorly conducting material. In contrast, the provision of a simple electrode in the hose is considered to be less effective.

A disadvantage of the known solution is that by providing the spiral electrode the change of drills is influenced strongly. In order to improve effectiveness a high voltage of about 15 kV is provided with such a solution.

A solution of this type can be taken from U.S. Pat. No. 5,667,565, for instance.

However, the provision of such a high voltage is dangerous particularly when tools are changed such that it is not surprising that this solution which was intended particularly for air-craft construction has not become established.

Further numerous attempts have become known to improve the removal of chips which are produced by drills or other cutting tools.

In this connection it has been suggested to separate the ionization process of the supplied air from the actual supply and, in this context, to ensure deionization of the chips with ionized indoor air. However, it has become evident that a very high air-handling capacity is necessary for this purpose which makes the realization considerably more expensive and which is in particular also noisy.

Further, it has already been suggested to replace the voltage used for ionizing the air by a particular ac voltage to reduce the required voltage to values which are not dangerous.

However, particularly with strongly electrically insulating materials such as PMMA deposits of chips often remain at the workpiece or the workpiece holder, or in or at the space surrounding these parts.

The document JP S62 284731 A1 discloses a method for removing the frictional electricity in a mechanical processing system and for preventing the chips from adhering to the remaining components.

DE 10 2013 005 871 A1 discloses a numerically controlled machining center, in particular a multi-axis drilling and milling center, comprising a multi-axis drilling and milling device having a vertical spindle.

CN104 096 696 A discloses a method and a device for machining a blank and for collecting the resulting chips.

SUMMARY OF THE INVENTION

Thus, the invention is based on the task of providing a dental machine tool according to the preamble of claim 1 which is improved with regard to the cleaning action of chip deposits, without producing particularly high noise levels, and wherein in particular chip deposits in the spaces or surfaces adjacent to the workpiece are avoided.

This task is inventively solved by claim 1. Advantageous developments may be taken from the subclaims.

According to the invention it is particularly favorable that a housing is provided to which the air nozzle is attached. The air nozzle can also be mounted in the housing, but according to the invention it is connected with the interior space of the housing by means of corresponding mechanical means. In this way, it is ensured initially that a tightly confined space is provided which considerably facilitates the ionization process in a surprising manner and which considerably improves the efficiency of ionization. Thus, in an inventively advantageous embodiment considerably lower voltages, such as for instance less than 8 kV, can be realized without risking an insufficient ionization process.

Even if the housing can be opened—and thus if contact with the air nozzle or the cover of the electrode is basically possible—the safety for instance with respect to unintentional contact from the outside—for instance by means of a conductive medium such as water—is reduced considerably. Moreover, in an advantageous embodiment a high series resistor of for instance 1 MW is provided which limits any current upon contact with living creatures to a non-dangerous degree of less than 10 mA. Furthermore, in an advantageous embodiment a cover of the electrode and/or the electrodes is provided which ensures protection against contact.

According to the invention it is also provided that, for a start, an air nozzle is directed towards the region which is particularly intensive or relevant in terms of chip deposits, that is to say the workpiece, the workpiece holder, the tool bank and/or a pane of a front flap of the machine tool. However, this alone is not enough and moreover it is provided according to the invention to align the at least one electrode for the generation of an electric field such that it is directed towards the side of the workpiece or the workpiece holder on which the tool machines the workpiece.

This means that the electrode ionizes specifically the air that is close to the machining side. Surprisingly, with the aid of the proper combination of these features complete ionization of the air and thus deionization of the chips can be realized to such an extent that they do not tend to deposit in corners of the housing in which many chips would collect per se, such that by means of the complete deionization of the plastic chips, in particular of the PMMA chips, these chips can be removed easily and completely by a negative-pressure source.

It is particularly favorable to realize the ionization of the air by means of a pulsed symmetrical square-wave voltage. In this way, air cations and air anions are produced at an even distribution and due to the electrostatic adhesion the air cations discharge the negatively charged chips, that is to say the chip anions, and the air anions discharge the chip cations in turn.

According to the invention the close proximity of the electrodes to the machining side is favorable, too, as then the tendency of the air ions to discharge one another is reduced to a minimum.

The inventive electrodes are preferably oriented such that the electrode ends in a tip which is received within the air nozzle in a recessed manner. This tip is then oriented in the desired manner. The electrode is preferably configured as a surface which extends in the air flow direction by several centimeters. For instance, it can be realized in a sleeve-like manner, wherein the air flows along the inside and the outside of the sleeve and comes into intensive contact with the electrode.

By means of appropriate air-flow related measures, such as flow fins, which serve to swirl the air within the nozzle, that is to say before it is discharged, the tendency of all of the air molecules to come into contact with the electrode and thus to ionize is increased further.

Preferably, the swirl subsequent to the contact of the electrode is finished immediately such that the air flows out of the nozzle in a laminar fashion and is then supplied to the machining region of the workpiece in an ionized manner in a continuous flow.

According to the invention it is particularly favorable that in particular highly insulating PMMA chips can be prevented inventively from being deposited in inner corners of the housing. The reason for this is that the deionization of the chips is realized immediately at the place of generation such that ionized chips are prevented from being located outside of the machining region and accordingly tend to adhere to surfaces.

In this respect, in an inventively advantageous embodiment a laminar continuous but not very intensive air flow is provided which makes it possible to provide sufficient time for deionizing the chips. This can be realized in a favorable manner by means of an aerial fog which is produced by a plurality of, for instance at least three, air nozzles, which is formed by the serial arrangement of tool bank, workpiece holder, and workpiece. Preferably, the air nozzles can also be offset from one another, for instance angularly offset or laterally offset, in order to ensure a targeted laminar air supply at low pressure which is as extensive as possible.

In this connection it can be sufficient, for instance, to supply air at a pressure of only 0.1 bar or at an air flow of only 20 l/min to the machining regions to still ensure complete chip removal.

In an inventively advantageous embodiment it is provided to configure the air supply in a pulsed manner. In this connection, a double function can be achieved, on the one hand swirling the chips—during the air impulse—and on the other hand better ionization in the rest phase. With the help of this surprisingly simple measure the efficiency of ionization of the chips can be improved further. Preferably, the impulse/pause ratio is between 1 to 2 and 1 to 10 and preferably approximately 1 to 3.

According to a further preferred embodiment it is provided to arrange a plurality of nozzles of which at least one nozzle is directed towards the workpiece and/or the workpiece holder and/or the tool and/or the tool bank and/or the pane of the front flap, and to control the nozzles separately.

In this way, zones which are further away could be pressurized with higher pressure and cleaned more easily.

It is particularly favorable in the realization of several nozzles which are parallel in terms of the air flow—if not oriented exactly in parallel—that surfaces of the machining area can be deionized, too. This also results in an improved cleaning effect as the surfaces charged in this respect also deionize the oppositely charged chips.

For controlling the deionization effect it is possible to control the air supply and/or the voltage at the deionization nozzles. In particular, a combination of these two parameters can be used for the control.

Preferably, a comparatively compact milling chamber in a corner of a chamber, for instance at the rear/bottom, is sucked off. Due to the considerable distance between the air nozzle(s) and the suction connection uniform air removal with a good cleaning effect for the adhering chips takes place.

BRIEF DESCRIPTION OF THE DRAWINGS

Further advantages, details and features may be taken from the following description of two exemplary embodiments of the invention in conjunction with the drawings, in which:

FIG. 5 shows a nozzle in top view with electrodes.

DETAILED DESCRIPTION

Figure 1:
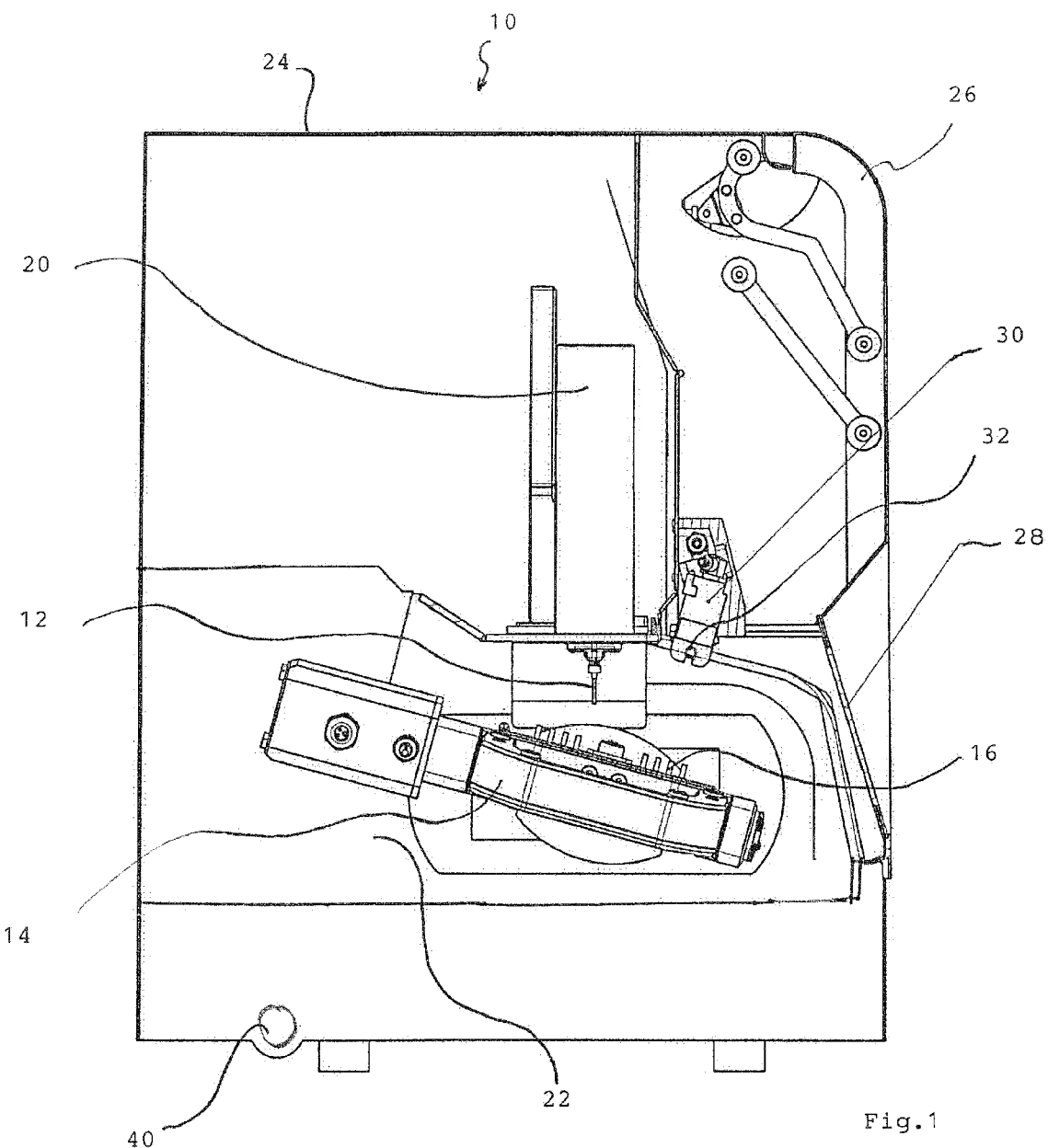
FIG. 1 shows a schematic side view of an inventive dental machine tool in one embodiment which is configured as a dental milling machine.

FIG. 1 shows a dental milling machine 10 having a tool 12, which is configured as a milling spindle in the exemplary embodiment illustrated, a workpiece holder 14, into which a workpiece (not illustrated) may be clamped, and a tool bank 16 which is attached to the workpiece holder in the case of the exemplary embodiment described herein.

In a way known per se both the tool with the tool drive 20 and the workpiece holder 14 can be moved multi-axially. In the exemplary embodiment illustrated the tool can be moved biaxially and the workpiece holder can be moved triaxially such that a five-axis dental milling machine is provided.

It is to be understood that instead any other machine tools may be realized, for instance four-axis or six-axis dental milling machines, drilling machines, grinding machines or any other machine tool which is used to effect machining.

The dental milling machine 10 comprises a milling chamber 22 which is substantially smaller than the remaining housing 24 of the dental milling machine 10, and for instance comprises one tenth to one third of the volume. The housing 24 of the dental milling machine 10 further comprises a door 26 which is equipped with a window 28 which is arranged in a slightly oblique fashion and tilted to the inside at the top and which makes possible to have a look at the workpiece during the machining process by the dental milling machine 10.

According to the invention, the air nozzle 30 comprises electrodes, one electrode 32 of which is schematically apparent in FIG. 1. The electrode 32 extends through the interior of the air nozzle 30 along the air line, that is to say parallel relative to the outflow direction, preferably along the entire length of the nozzle, in the exemplary case over about 4 cm. Opposite to it, that is to say offset by 180°, a further electrode is provided and the electrodes are connected to a voltage generator (not illustrated) which generates an electric voltage which can be controlled between 4 and 8 kV. FIG. 5 shows nozzle 30 with outflow channel 50 having electrodes 52, 54, disposed in a space-apart manner. Preferably, the electric voltage is an alternating voltage, namely a square-wave voltage, and preferably, one of the electrodes—namely the electrode which is not illustrated—is connected to ground.

In the exemplary embodiment illustrated, the air nozzle 30 is fixedly mounted to the housing, wherein it is to be understood that a movable installation is also possible alternatively, which carries along the air nozzle 30 with the tool 12—or the workpiece holder 14.

According to the invention, the air nozzle 30 comprises electrodes, one electrode 32 of which is schematically apparent in FIG. 1. The electrode 32 extends through the interior of the air nozzle 30 along the air line, that is to say parallel relative to the outflow direction, preferably along the entire length of the nozzle, in the exemplary case over about 4 cm. Opposite to it, that is to say offset by 180°, a further electrode is provided and the electrodes are connected to a voltage generator (not illustrated) which generates an electric voltage which can be controlled between 4 and 8 kV. Preferably, the electric voltage is an alternating voltage, namely a square-wave voltage, and preferably, one of the electrodes—namely the electrode which is not illustrated—is connected to ground.

The electrode 32 is arranged in the air nozzle 30 in a recessed manner such that protection against contact is provided in this connection. Moreover, the electrode 32 is connected with the voltage generator via a series resistor of at least one megohm.

Although in FIG. 1 only one air nozzle 30 is illustrated, it is to be understood that in fact a plurality of electrodes is provided. These electrodes are mounted next to one another or one after the other, that is to say above the drawing plane or below the drawing plane, and oriented towards one another obliquely, respectively. The preferred inclined position of the air nozzles strongly depends on the expanding cone of the air flow leaving the air nozzles 30 and amounts to particularly between 5° and 30°.

Preferably, at least one of the air nozzles is also directed towards the pane or the window 28 obliquely from the side, such that an air flow is produced which flows along the window 28.

The air nozzles extend substantially parallel to the tool spindle 12 from the top to the workpiece which is not illustrated and which is held clamped in the workpiece holder 14. This allows for direct and targeted air supply of ionized air to the position at which the chips are produced.

Chips are produced during the machining process of the machine tool 10. If, for instance, a plastic disc, such as a disc made of PMMA, is machined, charged chips are produced by means of the frictional electricity. They adhere to the disc clamped in the workpiece holder, said disc forming the workpiece, but also to the milling cutter as the tool 12 and in particular to the shanks of the tools received within the tool bank 16.

By means of the targeted supply of deionized air from the air nozzles 30 the chips adhering thereat are deionized in this way and can be removed easily by the air flow in one go.

This also applies to chips which adhere to the window 28; here, too, the chips are both deionized and carried along by the flow.

In one corner of the milling chamber 22 a negative-pressure connection 40 is provided which serves to suck off the chips. The deionized chips are sucked off together with the air supplied by the air nozzles 30 by means of the negative-pressure connection 40 and are thus completely removed from the milling chamber 22.

Figure 2:
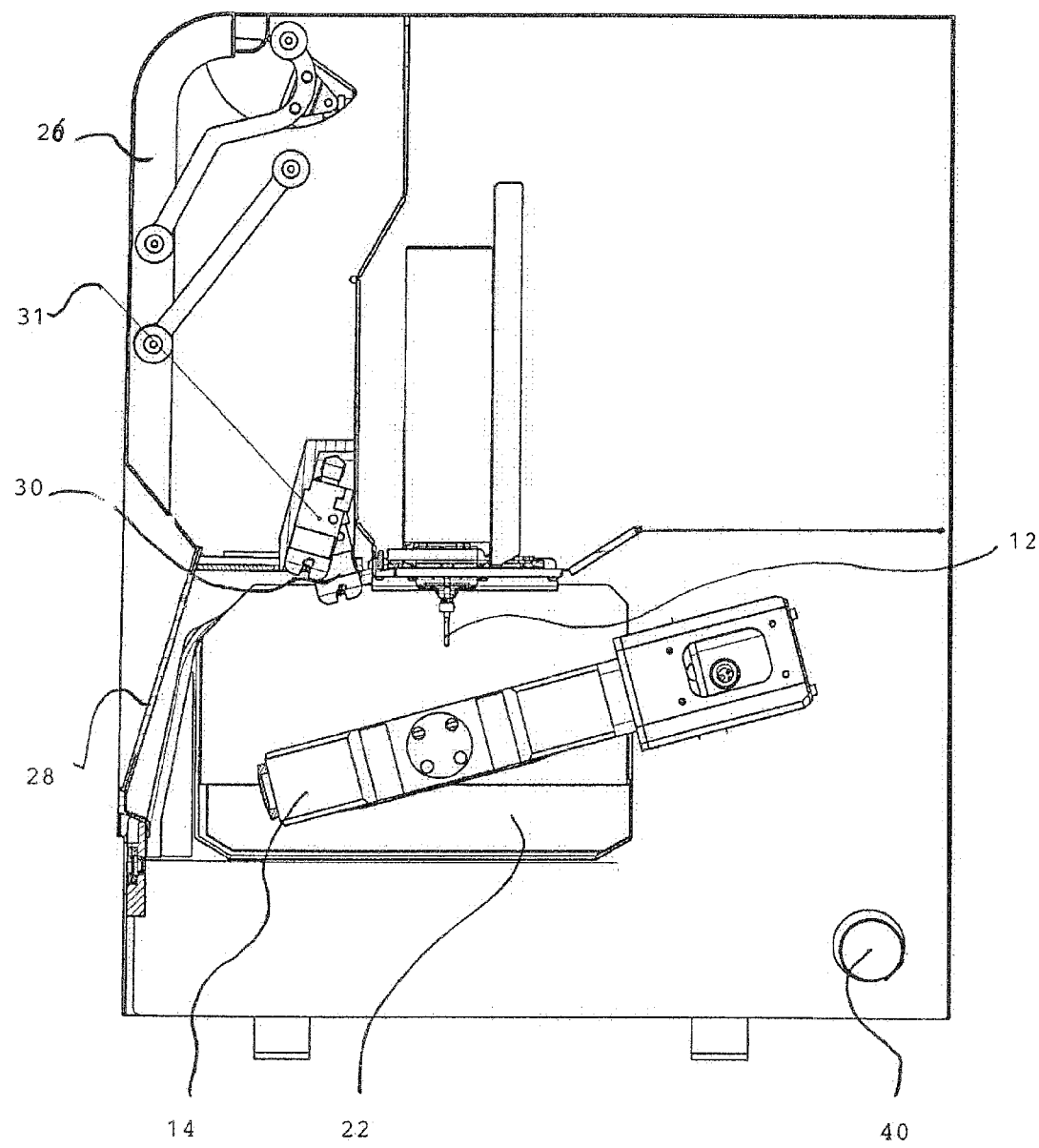
FIG. 2 shows an embodiment modified compared with the embodiment of FIG. 1, but in another side view.

In FIG. 2, a modified embodiment compared to the embodiment of FIG. 1 is apparent. Here, the negative-pressure connection 40 is arranged at a slightly different location, and two air nozzles 30 and 31 extend slightly obliquely to one another, as illustrated.

In the illustrated tool position, the flow axis of the air nozzle 30 is directed to an area just next to the machining position of the tool spindle 12 at the workpiece which is not illustrated, namely towards the door 26 or the window 28. In the exemplary embodiment illustrated, the workpiece holder 14—and thus the workpiece clamped therein—extends perpendicularly to the outflow direction of the air nozzle 30. The workpiece holder 14 is moved regularly during the machining process such that only an instantaneous position is indicated in this connection. A slightly oblique air supply to the workpiece through the air nozzle 30 is preferred in order to provide for a better air flow to remove the chips. Here, an inclination angle of 10° or 40° relative to the position illustrated in FIG. 2 is enough.

It is also possible to provide a plurality of negative-pressure connections 40, for instance in the rear corners to the right- and to the left-hand side, at the bottom of the milling chamber 22, respectively.

Figure 3:
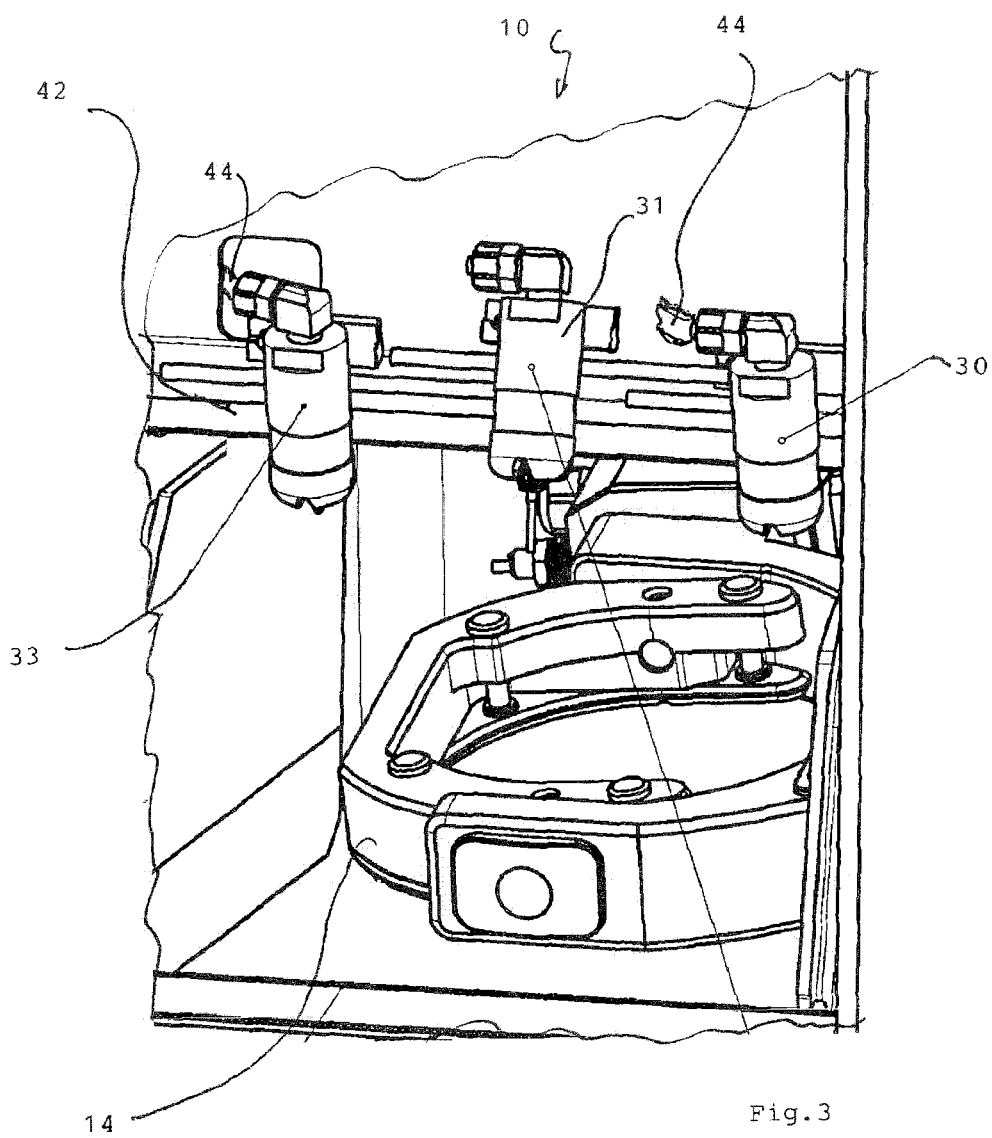
FIG. 3 shows a perspective view of a section of the dental milling machine according to the FIGS. 1 and 2.

From FIG. 3 a further embodiment of an inventive machine tool 10 is apparent. This embodiment shows three air nozzles 30, 31 and 33 which are mounted to an air nozzle holder 42 one next to the other and which are arranged relative to one another in an oblique fashion. The distance of the air nozzles 30, 31 and 33 is selected such that, in any case, the area of movement of the workpiece clamped in the workpiece holder 14 is covered by the added up outflow cone of the air nozzles 30, 31 and 33 during the machining process.

The air nozzles 30, 31 and 33 each comprise air connections 44 which are each connected to a positive-pressure source via hoses. Preferably, the pressure of the positive-pressure source is controllable and may amount to, for instance, between 0.1 bar and 1.0 bar, for instance to about 0.4 bar.

In an alternative embodiment it is provided to work with a comparatively high pressure of 5 bar to 7 bar. At this pressure, the length of throw of the emitted air is substantially higher, and distant areas of the milling machine, that is to say areas which are spaced apart from the respective nozzle, for instance, by 30 cm, may also be reached easily. In case of high-pressure nozzles of this type it is recommended to lengthen the ionization channel in order to ensure secure ionization of the air in spite of the higher outflow speed.

In one embodiment of the inventive dental machine tool it is provided to apply an operating voltage of 7 kV to the electrodes, namely at an impulse/pause ratio of between 0.5 to 1 and 2 to 1 using a square wave. The current between the electrodes or between the ionization electrode and the ground is limited to 0.5 mA such that no inadmissibly high current occurs even in case of comparatively humid air.

The area of the ideal air supply to the workpiece or tool is at a distance of between 50 mm and 250 mm in front of the nozzle.

A further advantage of the inventive solution is that the cleaning air flow is of comparatively low volume; at an air pressure of 1 bar it amounts to only 68 db measured at a distance of 60 cm next to the air nozzle.

In a modified embodiment it is provided to work with slightly lower pressure and to limit the current to 20 mA, and, in a third embodiment, to work with a lower voltage, for instance 4 kV and to limit the current to 2.5 mA.

The negative pressure of the negative-pressure connection may also be controllable, but preferably amounts to about 500 mbar.

Figure 4:
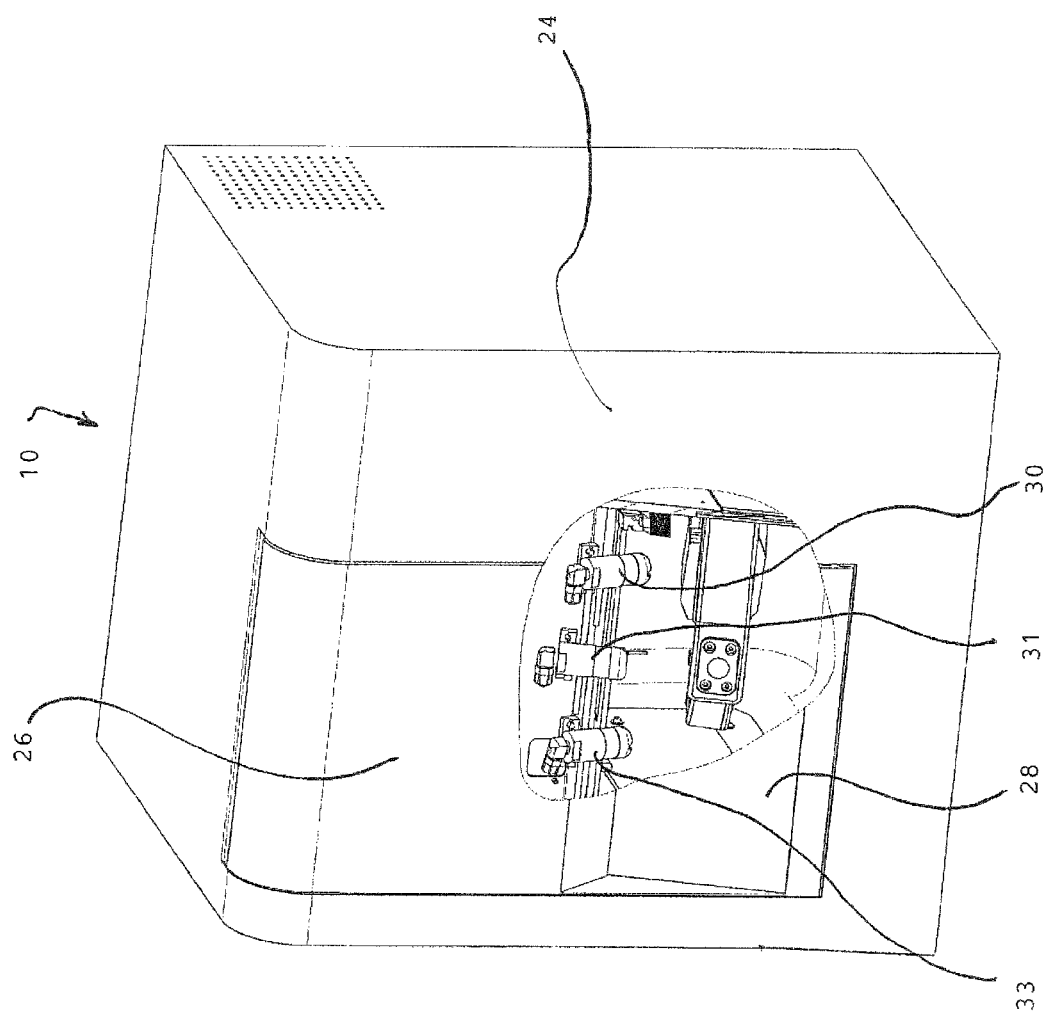
FIG. 4 shows a partially broken up perspective view of a dental milling machine according to the FIGS. 1 to 3.

From FIG. 4 a dental milling machine 10 is apparent in an embodiment according to FIG. 3, wherein, here, both the window 28 and the door 26 but also the housing 24 are illustrated partially broken up and allow to have a look at the nozzles 30, 31 and 33.

In this embodiment, the air nozzle 31 is directed such that its expanded air flow hits the window 28 obliquely from the side and deionizes any chips adhering thereto and carries them along such that they can be removed by means of the pressure connection 40.

The materials to be machined comprise all of the materials to be machined particularly in the dental field, and primarily the plastic materials PMMA, polyurethane, polyamide, PEEK and composites.

However, resins and plastic-modified resins may also be machined accordingly.

The invention claimed is:

1. A dental machine tool in a dental milling machine (10) comprising:
   a tool (12), wherein the tool (12) is changeable via a tool bank (16),
   a workpiece holder (14) for receiving a workpiece,
   a housing (24) which is closable during machining by the machine tool,
   a negative-pressure connection to the housing (24),
   a door (26) through which the workpiece and tool can be inserted and removed,
   wherein a plurality of air nozzles with at least one electrode each for generating an electric field in the region of each of the plurality of air nozzles or in front of each of the plurality of air nozzles are arranged next to one another and extend transversely over a front side of the housing (24) and over more than half the width of the dental machine tool,
   wherein at least one air nozzle (30) of the plurality of air nozzles is directed towards the workpiece and/or the workpiece holder (14) and/or the tool (12) and/or the tool bank (16) and/or a pane of a front flap of the machine tool, and comprising at least one electrode for generating an electric field in the region of the at least one air nozzle or in front of the air nozzle, and
   wherein at least one air nozzle comprising at least one electrode is directed towards that side of the workpiece or of the workpiece holder (14) on which the tool (12) machines the workpiece and
   wherein as a result, application of pulsating AC voltage provides spatial deionization of the air flowing through the housing (24) and/or deionization of the surfaces of the workpiece, workpiece holder (14), tool (12) and/or window (28) and of the chips produced by the machining operation.

2. The dental machine tool as claimed in claim 1, characterized in that the at least one electrode is connected with a voltage generator which produces an electric voltage of more than 1 kV.

3. The dental machine tool as claimed in claim 2, characterized in that the at least one electrode voltage is between 4 and 8 kV.

4. The dental machine tool as claimed in claim 1, characterized in that a voltage generator which is connected with the at least one electrode produces an AC voltage.

5. The dental machine tool as claimed in claim 4, characterized in that a voltage generator produces a square-wave voltage.

6. The dental machine tool as claimed in claim 1, characterized in that the machine tool comprises a door (26) through which the workpieces and tools can be inserted and removed, and in that the at least one air nozzle (30) with the at least one electrode is arranged above the door.

7. The dental machine tool as claimed in claim 6, characterized in that the dental machine tool comprises a window (28) in the housing (24) or in a door (26) of the housing, and in that the outflow direction of at least one air nozzle (30) is directed towards the window (28).

8. The dental machine tool as claimed in claim 6, characterized in that the at least one electrode is arranged adjacent to the door.

9. The dental machine tool as claimed in claim 1, characterized in that at least one air nozzle (30) is equipped with at least one electrode or two electrodes and that at least one air nozzle (30) outputs air in an air nozzle (30) which is directed towards the workpiece and/or the tool (12).

10. The dental machine tool as claimed in claim 1, characterized in that the at least one electrode forms part of an ionizer, and that an air flow channel extends between the at least one air nozzle (30) and the negative-pressure connection of the housing (24), and that the ionizer is directed towards the air flow channel, upstream of the tool/workpiece.

11. The dental machine tool as claimed in claim 1, characterized in that at least one air nozzle (30) is directed towards shanks of the tools in a tool bank (16).

12. The dental machine tool as claimed in claim 1, characterized in that each air nozzle (30) which is equipped with at least one electrode comprises two opposite electrodes which extend in the form of a partial ring around an outflow channel which is configured between 0.5 cm and 5 cm in front of the air nozzle (30), and that the electrodes deionize the air flow over a distance of more than 1 cm.

13. The dental machine tool as claimed in claim 12, characterized in that the distance comprises at least 5 cm.

14. The dental machine tool as claimed in claim 1, characterized in that the at least one air nozzle (30) or the plurality of air nozzles is connected to an air control unit which changes the air flow considered over time and gives off air impulses.

15. The dental machine tool as claimed in claim 1, characterized in that via the air nozzle (30) or the air nozzles which are equipped with ionizing electrodes a defined air flow is generated which is directed towards the workpiece, the workpiece holder (14), the tool (12) and/or the tool bank (16), said air flow carrying off the chips produced by the machining process of the machine tool from the generation zone and supplying the chips to the negative-pressure connection.

16. The dental machine tool as claimed in claim 1, characterized in that several air nozzles are arranged transversely relative to the front flap of the dental machine tool in at least one row, offset from one another and/or offset angularly.

17. The dental machine tool as claimed in claim 1, characterized in that the sucked off amount of air produced by the negative-pressure connection is larger than the amount of air supplied by the air nozzle or air nozzles and that the inner space of the housing (24) is under negative pressure compared to the ambient air.

18. The dental machine tool as claimed in claim 1, characterized in that the negative pressure at the negative-pressure connection is 50 mbar to 500 mbar compared to the ambient air and that the positive pressure of the positive-pressure source to which the at least one air nozzle is connected is more than 0.1 bar.

19. The dental machine tool as claimed in claim 18, characterized in that the positive pressure of the positive-pressure source to which the air nozzle (30) is connected is controllable.

20. The dental machine tool as claimed in claim 18, characterized in that the positive pressure of the positive-pressure source to which the at least one air nozzle is connected is about 0.4 bar.

21. The dental machine tool as claimed in claim 1, characterized in that the amount of air supplied by the positive-pressure source is between 10 and 150 l/min.

22. The dental machine tool as claimed in claim 21, characterized in that the amount of air supplied by the positive-pressure source is between 40 and 90 l/min.

23. The dental machine tool as claimed in claim 21, characterized in that the amount of air supplied by the positive-pressure source is between 60 and 70 l/min.

24. The dental machine tool as claimed in claim 1, characterized in that the at least one air nozzle (30) in the housing (24) is substantially diametrically opposed to the negative-pressure connection such that the air flow channel of the air flow produced by the air nozzle (30) and the negative pressure extends diagonally transversely through the housing (24).

25. The dental machine tool as claimed in claim 1, characterized in that the dental machine tool is a dental milling machine.

26. The dental machine tool as claimed in claim 1, characterized in that the workpiece comprises a dental blank made of ceramic, composite or plastics material.

27. The dental machine tool as claimed in claim 26, characterized in that the plastics material comprises PMMA (polymethyl methacrylate).

* * * * *